United States Patent
Hayakawa et al.

(10) Patent No.: US 7,699,466 B2
(45) Date of Patent: Apr. 20, 2010

(54) VISUAL TRAINING DEVICE AND VISUAL TRAINING METHOD

(75) Inventors: Tomoe Hayakawa, Koganei (JP); Norio Fujimaki, Koganei (JP); Hideo Eda, Koganei (JP)

(73) Assignee: National Institute of Information and Communications Technology, Tokyo (JP)

( * ) Notice: Subject to any disclaimer, the term of this patent is extended or adjusted under 35 U.S.C. 154(b) by 104 days.

(21) Appl. No.: 11/334,867

(22) Filed: Jan. 19, 2006

(65) Prior Publication Data

US 2006/0164597 A1 Jul. 27, 2006

(30) Foreign Application Priority Data

Jan. 21, 2005 (JP) .......................... P2005-013492

(51) Int. Cl.
*A61B 3/00* (2006.01)
*A61B 3/14* (2006.01)
*A61B 3/10* (2006.01)

(52) U.S. Cl. .................. 351/203; 351/209; 351/211

(58) Field of Classification Search .............. 351/200, 351/203, 209, 211
See application file for complete search history.

(56) References Cited

U.S. PATENT DOCUMENTS 5,139,323 A * 8/1992 Schillo .................. 351/45
5,852,489 A * 12/1998 Chen .................... 351/237
6,206,702 B1 * 3/2001 Hayden et al. ............ 434/236
6,464,356 B1 * 10/2002 Sabel et al. .............. 351/203
2007/0182928 A1 * 8/2007 Sabel .................... 351/224

FOREIGN PATENT DOCUMENTS

| JP | 08-294070 | 11/1996 |
| JP | 10-324636 | 12/1998 |
| WO | 03/065964 | 8/2003 |
| WO | 03/092482 | 11/2003 |

* cited by examiner

*Primary Examiner*—Scott J Sugarman
*Assistant Examiner*—Dawayne A Pinkney (57) ABSTRACT

A visual training device 1 including: a screen arranged facing a subject H having visual impairment; a line of vision detection unit that detects a line of vision of the subject H and outputs line of vision signals indicating the line of vision; a visual field data storage unit that stores visual field data indicating the visible area AR2 and the area of visual impairment AR1 of the subject H; and a screen control unit 53 that, on the aforementioned screen, moves the visible area AR2 specified based on the aforementioned visual field data in correspondence to the movement of the line of vision of the subject H specified by the aforementioned line of vision signals. The display format of the visible area AR2 or a region including the vicinity thereof, is displayed different from the display format of the other region. By doing this, an attitudinal barrier of the person with visual impairment, the subject, can be removed, and the visual training device can allow easy training to be provided.

10 Claims, 7 Drawing Sheets

VISUAL TRAINING DEVICE AND VISUAL TRAINING METHOD

BACKGROUND OF THE INVENTION

1. Field of the Invention

The present invention is related to a training device to improve the visual performance of visually impaired persons, specifically, visually impaired persons who have a partial impairment of their visual field.

2. Description of Related Art

Visual impairment may occur for a variety of reasons with approximately 10% of known cases caused by accidents, and approximately 60% caused by disease. In the past, many different therapies such as surgeries and drugs have been conducted in order to improve this form of visual impairment, as indicated in Japanese Unexamined Patent Application No. H10-324636.

Visual impairment can have a variety of symptoms, in addition to those cases where the entire visual field is completely occluded by, for example, a functional impairment of the eye or brain, there may also be cases of visual impairment of only one part of the visual field while vision is physically possible in the other regions.

Among the people thought to be completely blind due to visual impairment, there are in fact a large percentage of people who have a partially physically occluded field of vision (notably in the line of vision), and who are consciously convinced that they cannot see or have difficulty seeing beyond their actual ability to see.

This kind of person can be convinced that he or she "cannot see" or has "difficulty seeing." Attempts are being made to greatly improve visual capacity by reforming that attitude, for example, by training to look to the side of the visual point.

SUMMARY OF THE INVENTION

Nonetheless, changing this attitude of "I cannot see" is extremely difficult, and the desired effect cannot be obtained because this attitude obstructs corrective training. For example, even when pointing out the landscape in front of the visually impaired and giving the advice that "since this is the part that you should be looking at, do your best to look to the side of the line of vision," because this is not based on objective fact from the perspective of the visually impaired person, the previously described attitude of "I cannot see" often wins out, the advice is not received in a straightforward manner, and the training does not produce results.

Further, there is also the problem that, in spite of giving the visually impaired person advice on techniques for seeing in the direction of the line of vision, it becomes difficult to give accurate advice because the trainers cannot objectively comprehend the line of vision of the visually impaired person.

Thus, after studying the above points, the present invention addresses these issues by offering a visual training device that addresses the attitudinal barriers of visually impaired persons, and simplifies training of such persons.

Specifically, the visual training device related to the present invention, is characterized by having a screen arranged to face a subject with visual impairment; a line of vision detection units that detect a line of vision of the subject and outputs a line of vision signals indicating the line of vision; a visual field data storage unit that stores visual field data indicating the visible area and the area of visual impairment of the subject; and a screen control unit that, on the aforementioned screen, moves the visible area specified based on the aforementioned visual field data in correspondence to the movement of the line of vision of the subject specified by the aforementioned line of vision signals, and thereby makes the displayed format of the visible area or the region including the vicinity thereof different from the display format of another region in order to promote the awareness of the subject.

The visual training method related to the present invention is characterized by: arranging a screen facing a subject with a visual impairment; detecting the line of vision of the subject via a line of vision detection units; storing, in a visual field data storage unit set up in a specified region of memory visual field data indicating the visible area and the area of visual impairment in the visual field of the subject; and moving on the aforementioned screen the visible area specified based on the aforementioned visual field data in correspondence to the movement of the line of vision of the subject specified by the line of vision signals output from the aforementioned line of vision detection units, and thereby making the display format of the visible area or the region including the vicinity thereof different from the display format of another region.

Further, the aforementioned visual field data must be acquired ahead of time by testing the subject, etc. and storing the same.

Thus, the visual field that the subject should physically be able to see can be readily understood by a third party, for example, by a trainer, and because the subject must also recognize that the understanding is based on images acquired from visual field data and line of vision signals and is objectively correct, the subject cannot escape into a subjective attitude of "I cannot see." In other words, for example, in relation to the advice from the trainer, etc. that "you should be able to see this now," this must be accepted compliantly, and this becomes a training incentive for the subject, and heightens the motivation for training. Then, as a result, effective training can take place, parts thought to be not seeable become seeable, and the visual capacity of the subject can be effectively improved.

The aforementioned screen control unit displaying images that the subject can recognize, and displaying nothing in the region in an aforementioned other region can be cited as a concrete embodiment. Here, in addition to painting with one color such as black or white, etc. "displaying nothing" also includes displaying something with no meaning such as a row of graphics. An image that the subject can recognize also includes, for example, painting with one specified color. This is because the color can cause recognition.

To confirm whether the subject actually recognizes the display on the screen, the recognized image may be orally reported to the third party, if a third party is involved, but if, for example, the subject is working alone, it is preferable that a response signal receiving unit be further provided to receive response signals indicating the response from the subject viewing the screen. The response signals received by the response signal receiving unit may also be determined automatically by a computer.

To cite a more preferable example, the aforementioned screen control unit would display on the screen a virtual space that imitates an actual scene etc., and that virtual scene image would be moved corresponding to response signals relating to directional indications received from the subject by the aforementioned response signal receiving unit, allowing the subject to have a pseudo-moving experience in the virtual space. This kind of arrangement could be suitable for providing training that can be directly tied to real life experiences.

According to the present invention, the part that the subject should physically be able to see can be understood by a third party, for example, by a trainer, and because the subject must also recognize that the understanding is based on images acquired from visual field data and line of vision signals and is objectively correct, the subject cannot escape into the subjective attitude of "I cannot see." In other words, for example, in relation to the advice from the trainer, etc. that "you should be able to see this now," this must be accepted compliantly, and this becomes a training incentive for the subject, and heightens the motivation for training. Then, as a result, effective training can take place, parts thought to be not seeable become seeable, and the visual capacity of the subject can be effectively improved.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

An embodiment of the present invention will be explained below by referring to the diagrams.

Figure 1:
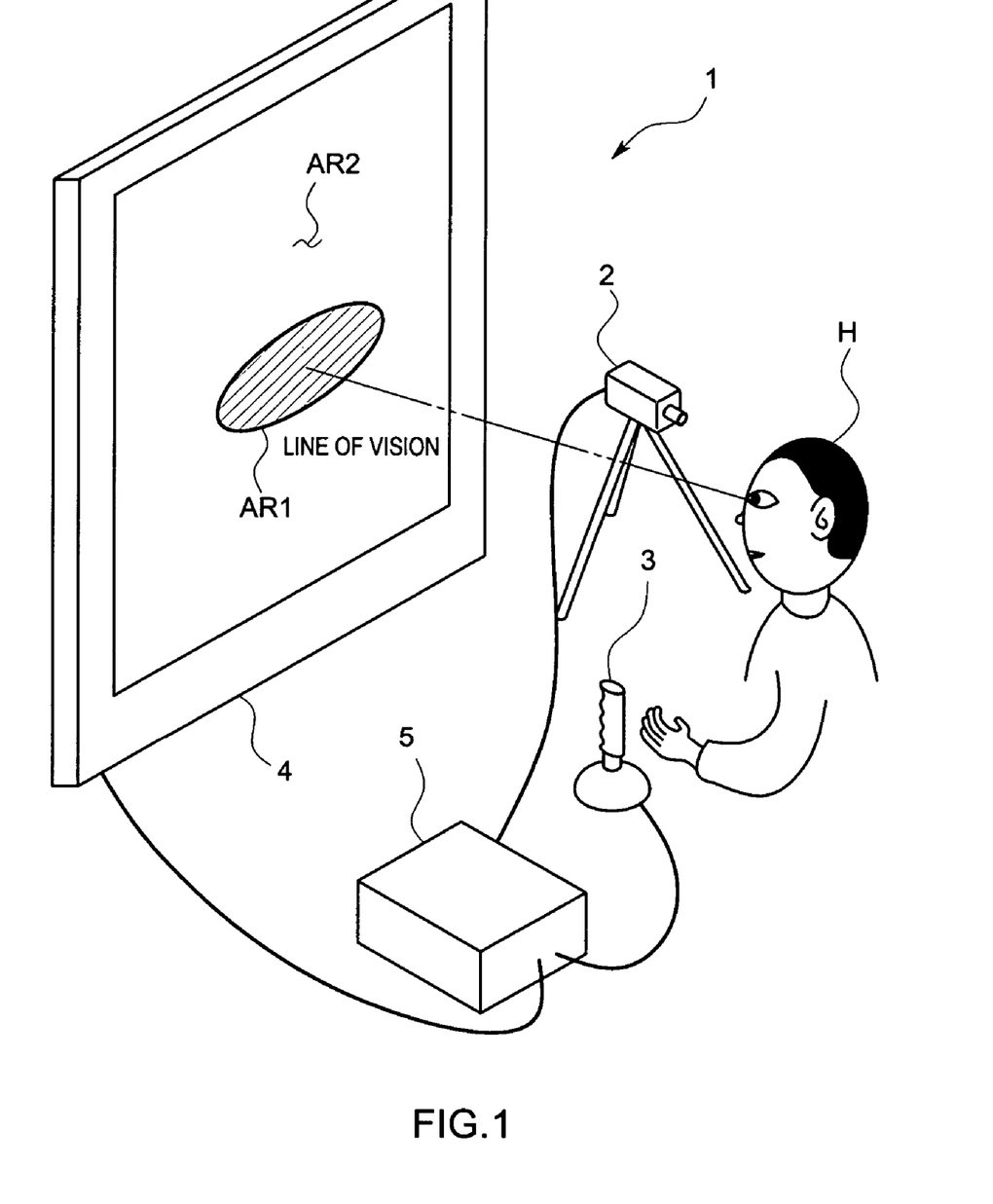
FIG. 1 is a schematic diagram indicating the entire visual training device of an embodiment of the present invention.

As schematically indicated in FIG. 1, a visual training device 1 related to the present embodiment comprises a line of vision detection unit or means 2 that measures the line of vision of the subject H, an input member or means 3, a display screen 4, and a data processing device 5.

Figure 3:
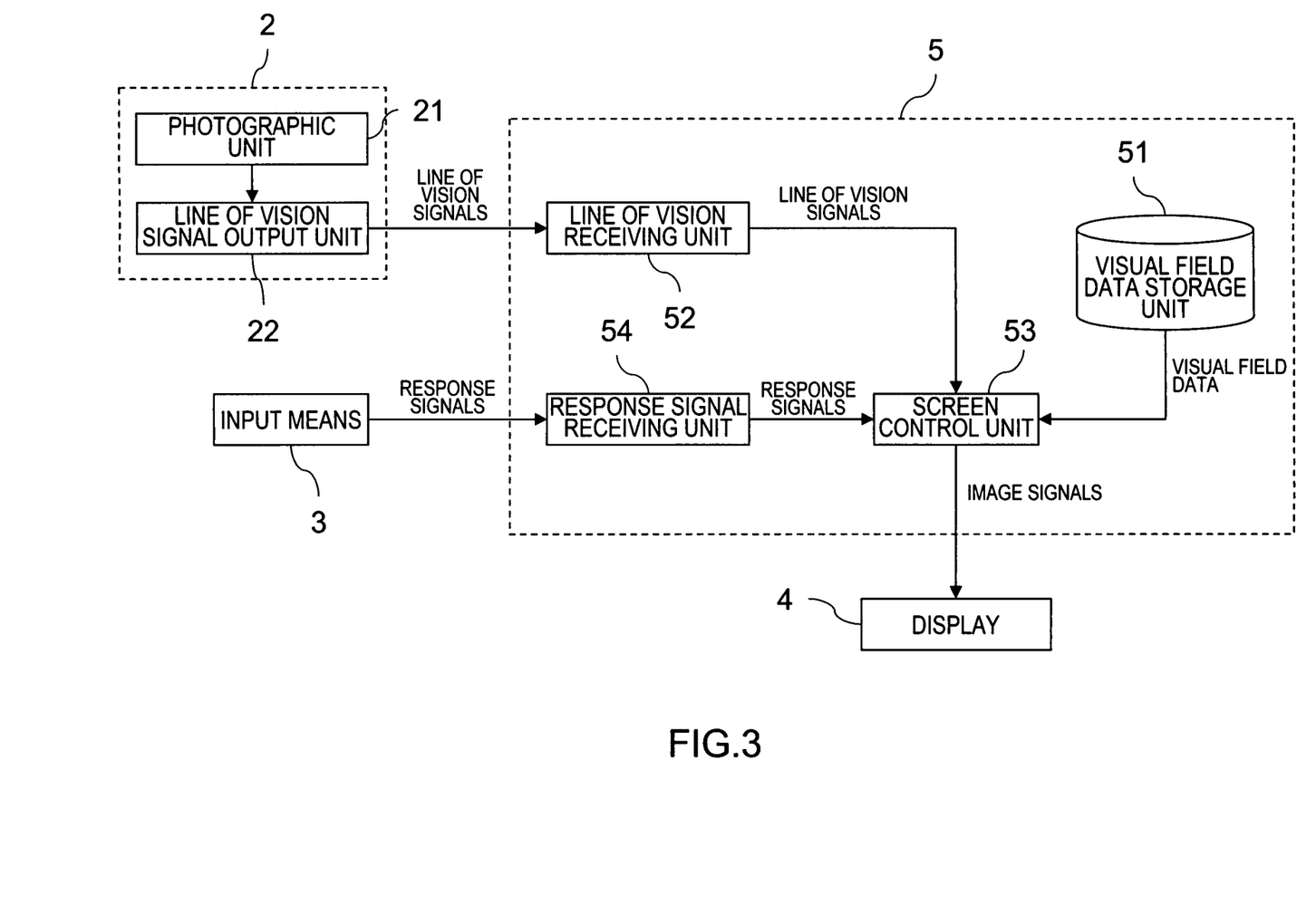
FIG. 3 is a functional block diagram indicating the configuration of functions of the data processing device of the same embodiment.

As indicated in FIG. 3, for example, the line of vision detection unit 2 comprises a photographic unit 21 such as a CCD camera that photographs the eyeball of the subject H, and a line of vision signal output unit 22 that processes the image data output from the photographic unit 21, calculates a line of vision from a center of gravity position of the iris and pupil, and outputs this as line of vision signals. Further, the data processing device 5 may also carry out the functions as this line of vision signal output unit 22.

The input member 3 configured as a mouse, joystick, controller or keyboard, etc. that can be manipulated by the subject H. When manipulated by the subject H, this operational form is transmitted to the data processing device 5 as response signals from the subject H, which will be described later.

The display screen 4 is, for example, a CRT display, a liquid crystal display, or a plasma display, etc., and displays on that screen images corresponding to image signals sent from the data processing device 5.

Figure 2:
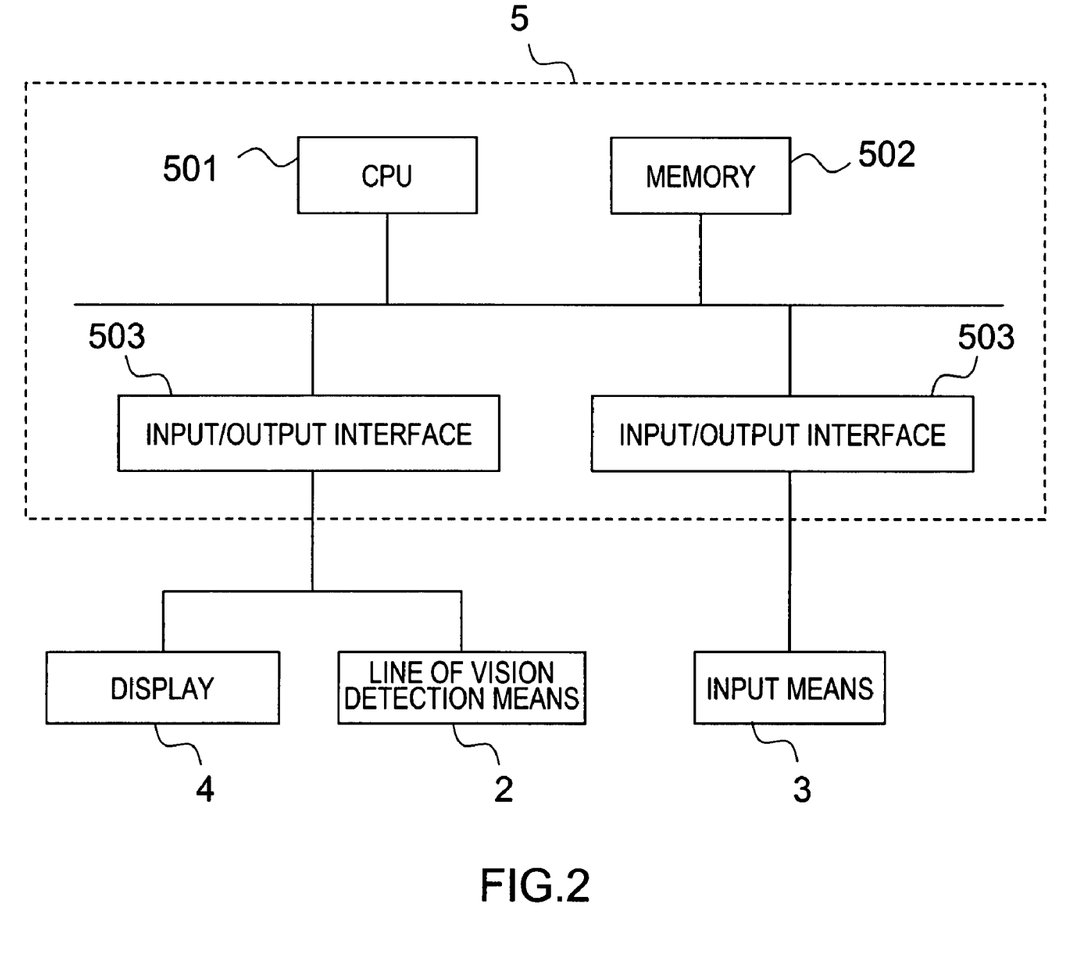
FIG. 2 is a schematic diagram indicating the configuration of the equipment of the data processing device of the same embodiment.

The data processing device 5 is, for example, a general purpose or customized computer, and as indicated in FIG. 2, structurally comprises a CPU 501, a memory 502, and an input/output interface 503. Then, as indicated in FIG. 3, by the aforementioned units 501 to 503 operating together based on a specified program stored in the aforementioned memory 502, a visual field data storage unit 51, a line of vision signal receiving unit 52, a screen control unit 53, and a response signal receiving unit 54, etc. become manifest. These parts are realized by utilizing a program, but of course, is also possible to form them with discrete circuits without using the CPU 501 and memory 502, and in this sense, the visual field data storage unit 51, the line of vision signal receiving unit 52, the screen control unit 53, and the response signal receiving unit 54 may be interchangeably called a visual field data storage circuit, the line of vision signal receiving circuit, the screen control circuit, and the response signal receiving circuit respectively.

Next, the aforementioned units 51 to 54 will be described in detail.

The visual field data storage unit 51 is set up in a specified region of the aforementioned memory 502, and stores visual field data indicating the visible area AR2 and the area of visual impairment AR1 of the visual field of the subject H. More concretely, the visual field data is data acquired by specified testing of the subject H in advance, and the visual field data acquired this way is linked with identifiers of the subject H, separately input or imported, and is stored in the visual field data storage unit 51.

The line of vision signal receiving unit 52 receives line of vision signals from the aforementioned line of vision detection unit 2, and temporarily stores these in a specified region of the memory 502 (comprising a buffer and a latch, etc.).

The screen control unit 53 acquires the aforementioned visual field data and line of vision signals, generates image signals based on these, and outputs the image signals to the display screen 4 which can be part of an image generating unit. The screen control unit 53 can move the aforementioned visible area AR2 specified from the visual field data, on the aforementioned screen corresponding to the movement of the line of vision of the subject H specified by the aforementioned line of visions signals, and also causes the display format of that visible area AR2 to differ from the display format of the other region, specifically, the area of visual impairment AR1 in order to promote an awareness in the subject H.

In this embodiment, for example, the area of visual impairment AR1 is painted with one fixed color (black). The display format of the visible area AR2 can be set and modified in multiple stages corresponding to the visual capacity and training progress of the subject H.

Figure 4:
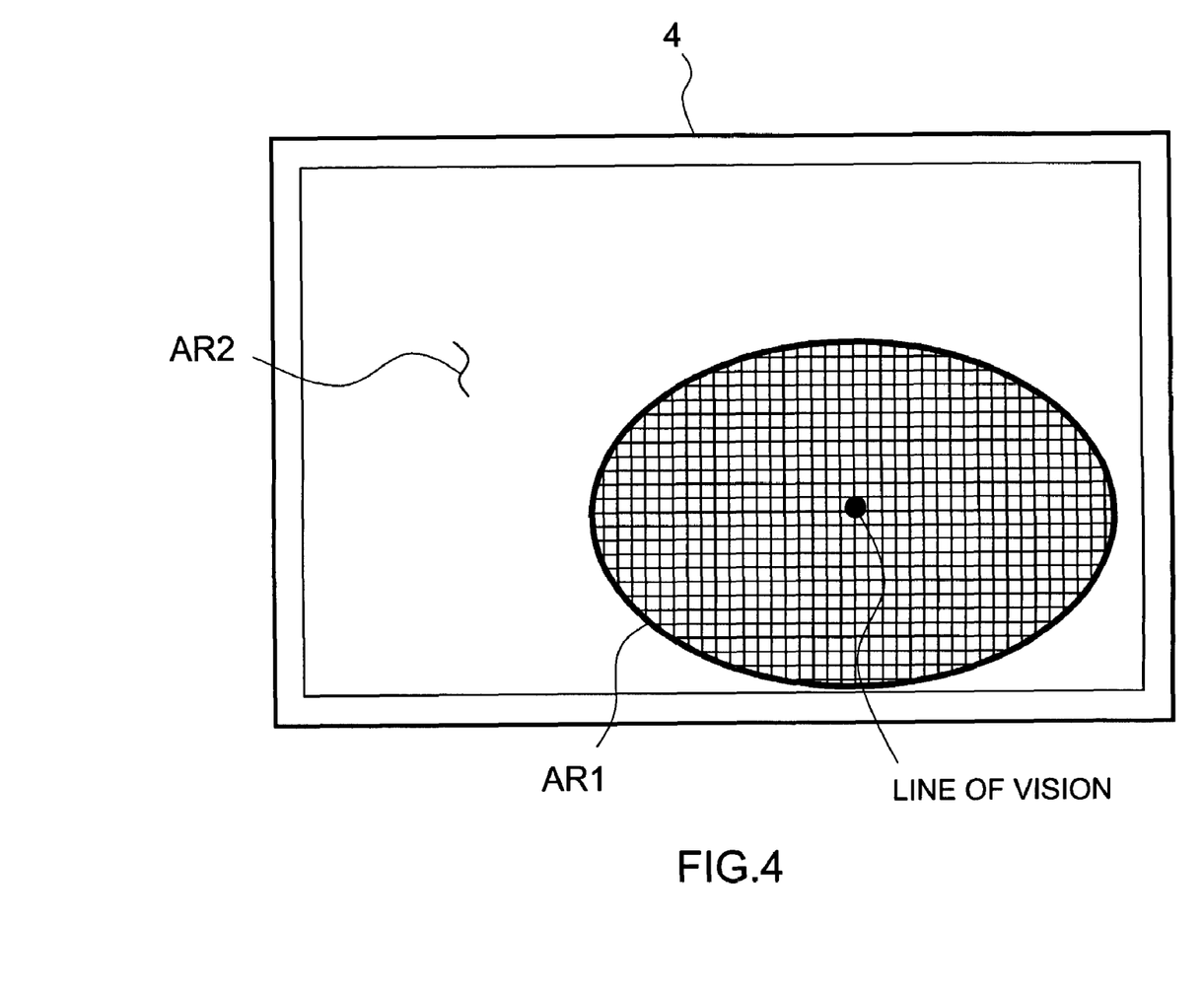
FIG. 4 is a screen example diagram indicating an example of a display format of the screen of the same embodiment.

In explanation, the first stage displays the entire visible area AR2 as painted with one color that is different from the color of an area of the visual impairment AR1 as indicated in FIG. 4 for example. The subject H can be trained to recognize this color by concentrating on the awareness of the visible area AR2.

Figure 5:
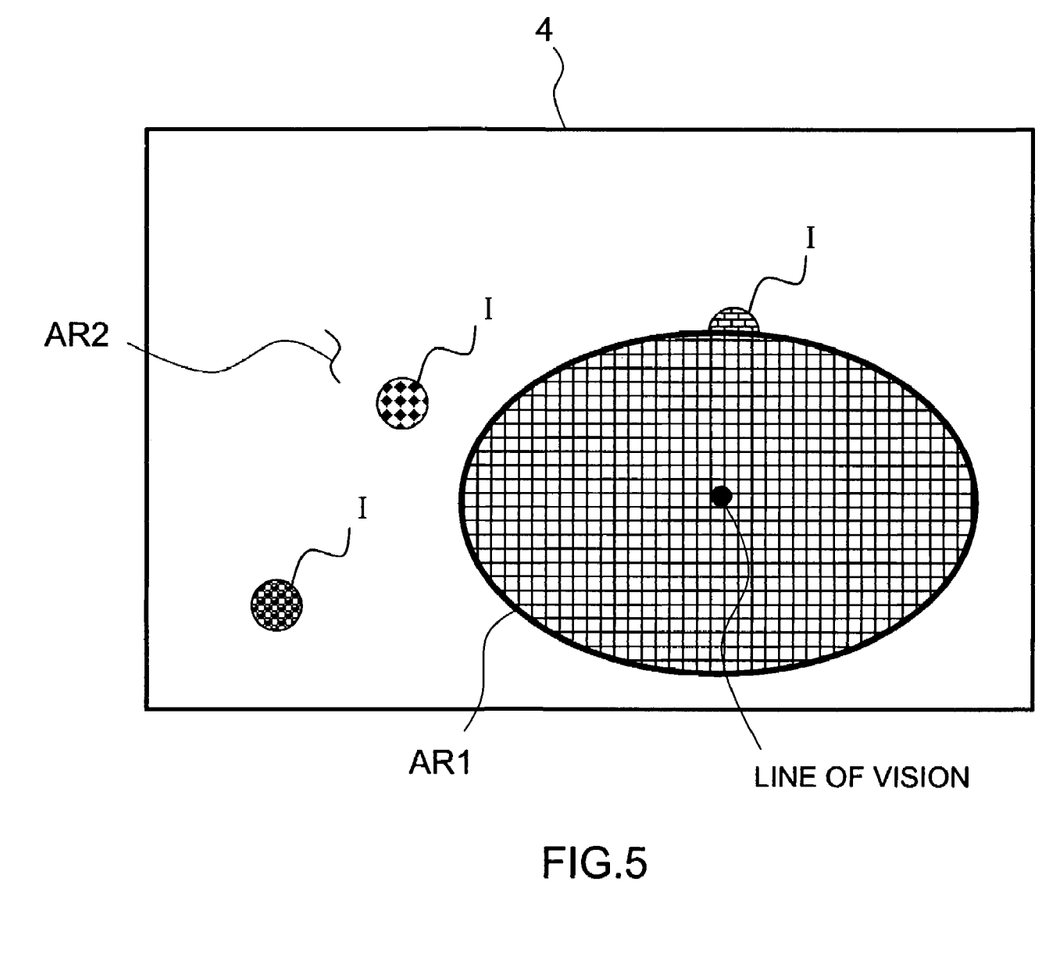
FIG. 5 is a screen example diagram indicating an example of a display format of the screen of the same embodiment.

The second stage displays complex images by letters and graphics by making a specified region I on the screen a fixed color, and causing this part I to flash, as indicated in FIG. 5 for example. The subject H positions the aforementioned image, etc. within the visible area AR2 by moving his/her own line of vision, and practices seeing this and recognizing its contents. Further, dynamic visual capacity can be trained by moving the aforementioned image, etc. on the screen.

Figure 6:
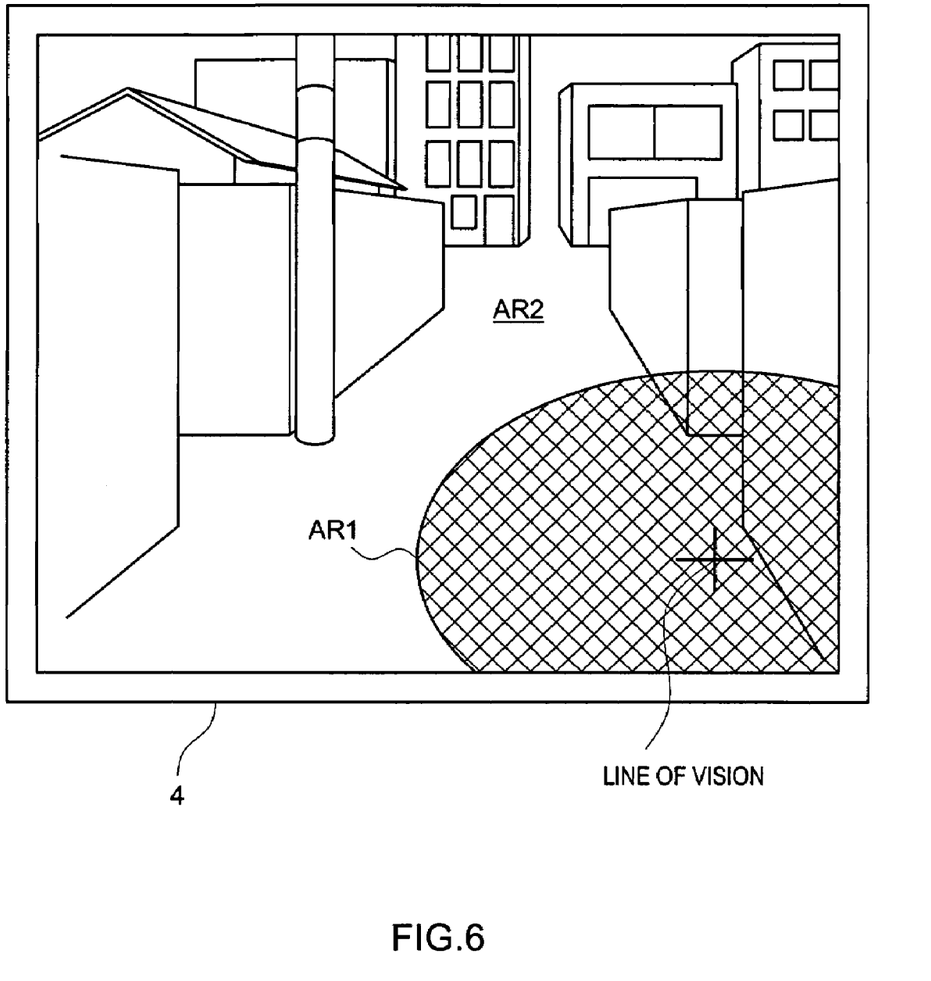
FIG. 6 is a screen example diagram indicating an example of a display format of the screen of the same embodiment.

The third stage displays an actual virtual space such as a scene, etc. at a specified region on the screen as indicated in FIG. 6 for example. The subject H can be trained to see within that virtual space by moving his/her own line of vision, and by broadening the visible area AR2 on the screen; and the subject H can be trained to move within that virtual space by using the input member 3.

The response signal receiving unit 54 receives input signals from the aforementioned input member 3 that the subject H manipulates while looking at the screen, specifically, response signals from the subject H, and stores them in a specified region of the memory 502 (comprising a buffer and a latch, etc.). The aforementioned screen control unit 53 and an audio control unit not indicated in the diagram, can read these response signals, and the display format of the screen can be changed and also audio signals are output corresponding to those contents.

Figure 7:
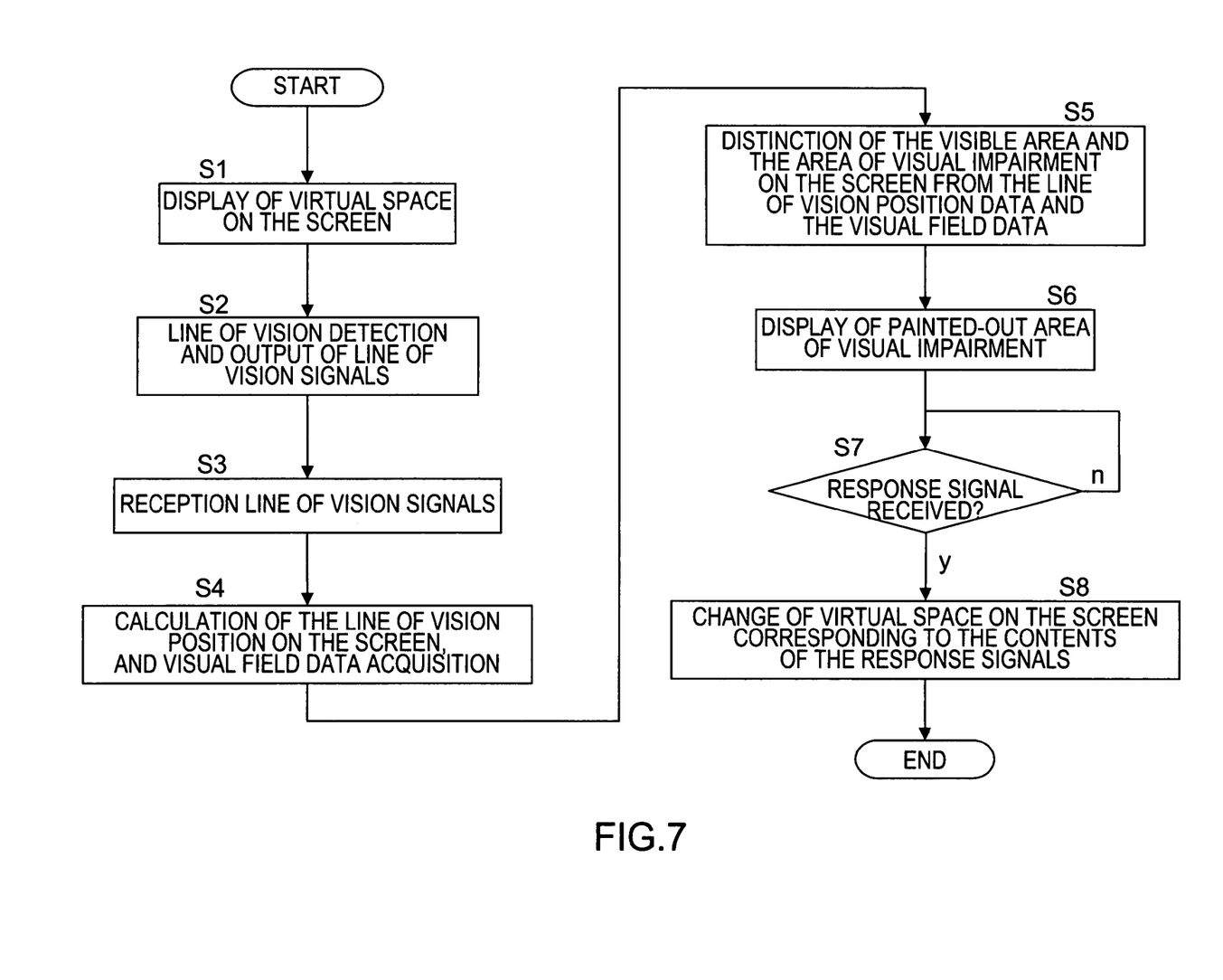
FIG. 7 is an operational flowchart of the visual training device of the same embodiment.

Next, the operation of a visual training device 1 with this kind of configuration will be explained below by referring to FIG. 7.

First, the subject H sits (of course, the subject may also stand) in a specified position facing the screen of the display 4. Meanwhile, the operator (a trainer or the subject H him/herself) confirms with the data processing device 5 who the subject H is by entering the identification number of the subject H. Next, the operator enters and sets the training stage, specifically, the display format of the visible area AR2. Assuming that the training area is set with multiple stages (3 stages) as previously described, here, for example, stage 3 will be set.

When the initial settings are completed in this way, the screen control unit 53 displays a virtual space like that indicated in FIG. 6 on the screen of the display 4 (step S1).

Meanwhile, the aforementioned line of vision detection unit 2 detects the direction of the line of vision of the subject H, and outputs this as line of vision signals (step S2).

When the line of vision signal receiving unit 52 receives these line of vision signals (step S3), the screen control unit 53 calculates from these line of vision signals where on the screen the line of vision of the subject is, and the visual field data of the subject H is acquired from the visual field data storage unit 51 (step S4). Then, based on the visual field data and the position data indicating the aforementioned center of the line of vision, the area of visual impairment AR1 and the visible area AR2 on the screen are distinguished (step S5), and as indicated in FIG. 6, the virtual space is displayed in the visible area AR2 as is, and the area of visual impairment AR1 is, for example, painted with the one color black, and nothing is displayed (step S6). In this way, if the line of vision of the subject H changes, the area of visual impairment AR1 on the screen moves correspondingly, and nothing is displayed in this region.

In this example, the area of visual impairment AR1 of the subject H is broadened by centering the line of vision, and the subject H can see the periphery around the line of vision. Consequently, by training to arrange the consciousness of seeing in the periphery that is not in the line of vision while practicing the technique of positioning the visible area AR2 in the main part of the screen, the subject H can comprehend this virtual space.

Next, if the subject H tilts the input member 3 (for example, a joystick controller) to the front and advances forward on the road, the response receiving unit receives the response signals from the input member 3 (step S7). Then, based on those response signals, the screen control unit 53 makes the computations, changes the virtual space on the screen, and gives a pseudo-experience which is similar to the subject H moving within the virtual space (step S8). Naturally, a noise, etc. can be generated if bumping into a wall, for example, further forward progress is ended, and the subject is informed that he or she has bumped into something.

According to the visual training device 1 configured in this way, the part that the subject H can physically see and the part that cannot be seen are displayed on the screen so as to be objectively determinable by a third party such as the trainer from the visual field data and the line of vision signals. Consequently, the subject H cannot escape into the subjective attitude of "I cannot see." In other words, for example, in relation to the advice from the trainer, etc. that "you should be able to see this now," this must be accepted compliantly, and this becomes an training incentive for the subject, and heightens the motivation for training. Then, as a result, effective training can take place, and parts thought to be not seeable become seeable, and the visual capacity of the subject can be effectively improved within the possible scope of the subjects visual capability.

Moreover, particularly in this embodiment, because a virtual space that imitates an actual scene is displayed on the screen and can allow the subject H to have a pseudo-moving experience in that virtual space, by setting up the virtual space in a location where the subject actually moves, the training can be directly tied to real life experiences that can be suitably conducted.

Further, in addition to training in this kind of virtual space, training can also be conducted in various stages by changing the display format on the screen, and therefore, suitable training corresponding to the visual capacity and training progress of the subject H can be conducted.

Further, the present invention is not limited to the aforementioned embodiment. For example, the image display region may be made up of the vicinity around the visible area AR2. In addition, various modifications may be made to the present invention without departing from the scope thereof.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A visual training device, which training includes changing a line of vision and looking to areas adjacent a visual point, comprising:

a screen arranged facing a subject with a visual impairment and visible to a third party;

a line of vision detection unit that detects the line of vision of the subject and outputs line of vision signals indicating the line of vision;

a visual field data storage unit that stores visual field data indicating a specific visible area that the subject can see completely and a specific area of visual impairment that the subject cannot see completely or partially;

a response signal receiving unit that receives response signals indicating the response from the subject viewing the screen; and a screen control unit that displays on the screen a specific image for visual training in the specific visible area and prevents the display of an image in the specific area of visual impairment, the screen control unit moving the specific visible area based on the visual field data in correspondence to the movement of the line of vision of the subject specified by the line of vision signals, wherein the screen control unit enables the third party to view the specific image for visual training in the specific visible area and to view the area of visual impairment superimposed over the specific image, wherein the screen control unit displays on the screen the specific image represented in a virtual space where the specific image imitates an actual scene that the subject would experience in real life, the virtual scene image is moved corresponding to the response signals relating to the directional indications received by the response signal receiving unit from the subject, and the subject is allowed a pseudo-moving experience within the visual space while the third party simultaneously views the relationship of the specific image and the area of visual impairment.

2. The visual training device according to claim 1 wherein the screen control unit displays the image in an almost entirely visible area on the screen.

3. The visual training device of claim 1 wherein the specific area of visual impairment includes areas that the subject cannot see completely and areas that the subject cannot see partially.

4. A visual training method, which training includes changing a line of vision and looking to areas adjacent a visual point, comprising:

arranging a screen facing a subject with a visual impairment and visible to a third party;

detecting the line of vision of the subject via a line of vision detection unit;

storing in a visual field data storage unit set up in a specified region of memory, visual field data indicating a specific visible area that the subject can see completely and a specific area of visual impairment in the visual field of the subject that the subject cannot see completely or partially;

using a computer to receive response signals indicating the response from the subject viewing the screen;

using a computer to display on the screen a specific image for visual training in the specific visible area and preventing the display of an image in the specific area of visual impairment, move on the screen the visible area specified based on the visual field data in correspondence to the selection of behavior or movement of the line of vision of the subject specified by the line of vision signals output from the line of vision detection unit, and to enable a third party to view the specific image for visual training in the specific visible area and to view the area of visual impairment; and using the computer to display on the screen the specific image represented in a virtual space where the specific image imitates an actual scene that the subject would experience in real life, the virtual scene image is moved corresponding to the response signals relating to the directional indications received by the response signal receiving unit from the subject, and the subject is allowed a pseudo-moving experience within the visual space while the third party simultaneously views the relationship of the specific image and the area of visual impairment.

5. The method of claim 4 further comprising providing an instruction to the subject regarding a visibility of features of the specific image for visual training in the specific visible area.

6. The method of claim 5 wherein the instruction is provided by the third party.

7. The method of claim 4 further comprising providing an instruction to the subject regarding a visibility of the specific image for visual training in relation to the specific area of visual impairment.

8. The method of claim 7 wherein the instruction is provided by the third party.

9. A visual improvement training device for subjects with limited fields of vision, which training includes changing a line of vision and looking to areas adjacent a visual point, comprising:

an image generating unit for providing images that can be viewed by a subject and a third party;

a line of vision detection unit to monitor an eye of the subject and provide signals indicative of the subject's line of vision relative to images viewed by the subject from the image generating unit;

a visual field data storage unit that stores visual field data including a first area indicating a specific visible area that the subject can see completely and a second area indicating a specific visual impairment field that the subject cannot see completely or partially;

a control unit that receives the signals indicative of the subject's line of vision and controls the image generating unit to provide specific images for visual training in the first area, and preventing the display of images in the second area from the visual field data storage unit in correspondence to the movement of the line of vision signals, the control unit also enabling a third party to view the first area and the second area, and displays on the screen the specific image represented in a virtual space where the specific image imitates an actual scene that the subject would experience in real life, wherein the virtual scene image is moved corresponding to the response signals relating to the directional indications received by the response signal receiving unit from the subject, and the subject is allowed a pseudo-moving experience within the visual space while the third party simultaneously views the relationship of the specific image and the area of visual impairment; and an input control member to enable the subject to change the images provided by the image generating unit to provide a pseudo moving experience within a virtual space.

10. A system for visual training, which training includes changing a line of vision and looking to area adjacent a visual point, comprising:

a screen facing a subject with a visual impairment and a third party;

a line of vision detection unit detecting a line of vision of the subject and outputting line of vision signals indicating the line of vision of the subject;

means for storing visual field data indicating a specific visible area that the subject can see completely and a specific area of visual impairment that the subject cannot see completely or partially;

means for displaying a specific image for visual training in the specific visible area and for preventing the display of an image in the specific area of visual impairment of the subject on the screen including boundaries between the specific visible area and the specific area of visual impairment;

means for relatively moving the area of visual impairment of the subject to the visible area based on the visual field data in correspondence with a movement of the line of vision of the subject specified by the line of vision signals;

means for displaying the specific image for visible training in the specific visible area and for preventing the display of an image to enable a third party to indicate to the subject features of the specific image that are recognizable in the visible area when the area of visual impairment is moved relative to the visible area based on the visual field data in correspondence to the movement of the line of vision of the subject specified by the line of vision signals, means for generating response signals indicating the subject's desire to change the image on the screen in a pseudo-moving experience;

means for receiving response signals from the means for generating response signals indicating the subject's desire to change the image on the screen in the pseudo-moving experience; and means for displaying on the screen the specific image represented in a virtual space where the specific images imitates an actual scene that the subject would experience in real life, allowing the subject the pseudo-moving experience within the virtual space while the third party simultaneously views the relationship of the specific image and the area of visual impairment, the virtual scene image moving in correspondence to the response signals received from the means for receiving response signals from the means for generating response signals indicating the subject's desire to change the image on the screen.

\* \* \* \* \*